United States Patent
Toth et al.

(10) Patent No.: US 7,113,570 B2
(45) Date of Patent: Sep. 26, 2006

(54) METHODS AND SYSTEMS FOR HELICAL OVERSCAN REDUCTION

(75) Inventors: Thomas Louis Toth, Brookfield, WI (US); Brian James Grekowicz, Salt Lake City, UT (US)

(73) Assignee: General Electric Company, Schenectady, NY (US)

( * ) Notice: Subject to any disclaimer, the term of this patent is extended or adjusted under 35 U.S.C. 154(b) by 46 days.

(21) Appl. No.: 11/053,801

(22) Filed: Feb. 8, 2005

(65) Prior Publication Data
US 2006/0177002 A1 Aug. 10, 2006

(51) Int. Cl.
*G21K 1/04* (2006.01)

(52) U.S. Cl. ............................ 378/150; 378/16; 378/20

(58) Field of Classification Search .................... 378/4, 378/15, 16, 20, 145, 147, 150, 151
See application file for complete search history.

(56) References Cited

U.S. PATENT DOCUMENTS

| 5,644,614 | A | 7/1997 | Toth et al. ................... 378/147 |
| 5,982,846 | A | 11/1999 | Toth et al. ..................... 378/19 |
| 6,023,494 | A * | 2/2000 | Senzig et al. ................... 378/4 |
| 6,173,039 | B1 * | 1/2001 | Hampel et al. ............. 378/150 |
| 6,385,279 | B1 | 5/2002 | Toth et al. ..................... 378/11 |

* cited by examiner

*Primary Examiner*—Courtney Thomas
(74) *Attorney, Agent, or Firm*—Carl B. Horton, Esq.; Armstrong Teasdale LLP

(57) ABSTRACT

Methods, apparatus and systems for controlling x-ray exposure during a scan with a computed tomography system are provided. The system includes an x-ray source, a collimator, and a detector array. The collimator includes a first cam configured to shutter an x-ray fan beam, generated by the x-ray source, in a first direction, a second cam located on an opposite side of a focal point of the x-ray source from the first cam, the second cam configured to shutter the x-ray fan beam in a second direction, the second direction being opposite from the first direction, and a cam drive configured to position at least one of the first cam and the second cam during the scan.

25 Claims, 7 Drawing Sheets

METHODS AND SYSTEMS FOR HELICAL OVERSCAN REDUCTION

BACKGROUND OF THE INVENTION

This invention relates generally to computed tomography (CT) imaging and, more particularly, to reducing x-ray exposure in a multislice CT imaging system.

In at least one known CT imaging system configuration, an x-ray source projects a fan-shaped beam which is collimated to lie within an X-Y plane of a Cartesian coordinate system and generally referred to as the "imaging plane". The x-ray beam passes through the object being imaged, such as a patient. The beam, after being attenuated by the object, impinges upon an array of radiation detectors. The intensity of the attenuated beam radiation received at the detector array is dependent upon the attenuation of the x-ray beam by the object. Each detector element of the array produces a separate electrical signal that is a measurement of the beam attenuation at the detector location. The attenuation measurements from all the detectors are acquired separately to produce a transmission profile.

In known third generation CT systems, the x-ray source and the detector array are rotated with a gantry within the imaging plane and around the object to be imaged so that the angle at which the x-ray beam intersects the object constantly changes. A group of x-ray attenuation measurements, i.e., projection data, from the detector array at one gantry angle is referred to as a "view". A "scan" of the object comprises a set of views made at different gantry angles, or view angles, during one revolution of the x-ray source and detector.

In an axial scan, the projection data is processed to construct an image that corresponds to a two dimensional slice taken through the object. One method for reconstructing an image from a set of projection data is referred to in the art as the filtered back projection technique. This process converts the attenuation measurements from a scan into integers called "CT numbers" or "Hounsfield units", which are used to control the brightness of a corresponding pixel on a display.

To reduce the total scan time required for multiple slices, a "helical" scan may be performed. To perform a "helical" scan, the patient is moved in the z-axis synchronously with the rotation of the gantry, while the data for the prescribed number of slices is acquired. Such a system generates a single helix from a fan beam helical scan. The helix mapped out by the fan beam yields projection data from which images in each prescribed slice may be reconstructed. In addition to reducing scan time, helical scanning provides other advantages such as better use of injected contrast, improved image reconstruction at arbitrary locations, and better three-dimensional images.

To further reduce the total acquisition time, multi-slice CT has been introduced. In multi-slice CT, multiple rows of projection data are acquired simultaneously at any time instant. When combined with helical scan mode, the system generates a single helix of cone beam projection data. Similar to the single slice helical weighting scheme, the projection data can be "weighted" prior to filtered back-projection. Thus, one technical effect is the generation of a volumetric CT three-dimensional (3D) image of a scanned object.

Multislice CT systems are used to obtain data for an increased number of slices during a scan. Known multislice systems typically include detectors generally known as 3-D detectors. With such 3-D detectors, a plurality of detector elements form separate channels arranged in columns and rows. Each row of detectors forms a separate slice. For example, a two slice detector has two rows of detector elements, and a four slice detector has four rows of detector elements. During a multislice scan, multiple rows of detector cells are simultaneously impinged by the x-ray beam, and therefore data for several slices is obtained.

In known CT systems, the x-ray beam from the x-ray source is projected through a pre-patient collimating device, or collimator, that defines the x-ray beam profile in the patient axis, or z-axis. The collimator includes x-ray absorbing material with an aperture therein for restricting the x-ray beam. The process of restricting the x-ray beam to the desired fan beam profile is termed "collimation".

With respect to restricting the x-ray beam, known collimators typically include two opposing metallic blades or eccentric cams that may be opened and closed to change the aperture width. The fan beam "thickness", as measured along the z-axis, can be selected by adjusting the blade or cam orientation. The blades or cams also may be moved in a same direction to displace the centerline of the aperture. Changing the aperture centerline changes the fan beam angle with respect to the z-axis.

When performing a helical scan with a multislice CT scanner, detector rows spiral into the image region sequentially and the x-ray exposure to rows outside of the image region are not used. That is, a z-axis length of the beam exceeds the z-axis length of images that are produced. This unused exposure, or dose occurs at both the beginning and end of a helical scan, and the amount of helical overscan increases with the width of the multislice detector.

BRIEF DESCRIPTION OF THE INVENTION

In one embodiment, a pre-patient collimator for controlling x-ray exposure during a scan with a computed tomography system is provided. The system includes an x-ray source and a detector array. The collimator includes a first cam configured to shutter an x-ray fan beam, generated by the x-ray source, in a first direction, a second cam located on an opposite side of a focal point of the x-ray source from the first cam, the second cam configured to shutter the x-ray fan beam in a second direction, the second direction being opposite from the first direction, and a cam drive configured to position at least one of the first cam and the second cam during the scan.

In another embodiment, a system for reducing x-ray exposure, or dose in a computed tomography system is provided. The system includes an x-ray source, a detector array including a plurality of detector cells extending in a z-axis, and a pre-patient collimator having a shutter cam and a tracking cam fabricated from an x-ray absorbing material, wherein the system is configured to determine a speed of a patient table along the z-axis, and position at least one of the shutter cam and the tracking cam during a scan using the determined table speed to define a thickness of a fan beam to be directed towards an object to be imaged.

In yet another embodiment, a method of controlling x-ray dosage in a computed tomography system is provided. The system includes a patient table translatable along a z-axis and a collimator having a first cam and a second cam that define an aperture. The method includes opening the first cam at a rate proportional to a translation speed of the table, and closing the second cam at a rate proportional to the translation speed of the table.

DETAILED DESCRIPTION OF THE INVENTION

As used herein, an element or step recited in the singular and proceeded with the word "a" or "an" should be understood as not excluding plural said elements or steps, unless such exclusion is explicitly recited. Furthermore, references to "one embodiment" of the present invention are not intended to be interpreted as excluding the existence of additional embodiments that also incorporate the recited features.

Also as used herein, the phrase "reconstructing an image" is not intended to exclude embodiments of the present invention in which data representing an image is generated but a viewable image is not. Therefore, as used herein the term "image" broadly refers to both viewable images and data representing a viewable image. However, many embodiments generate (or are configured to generate) at least one viewable image.

Figure 1:
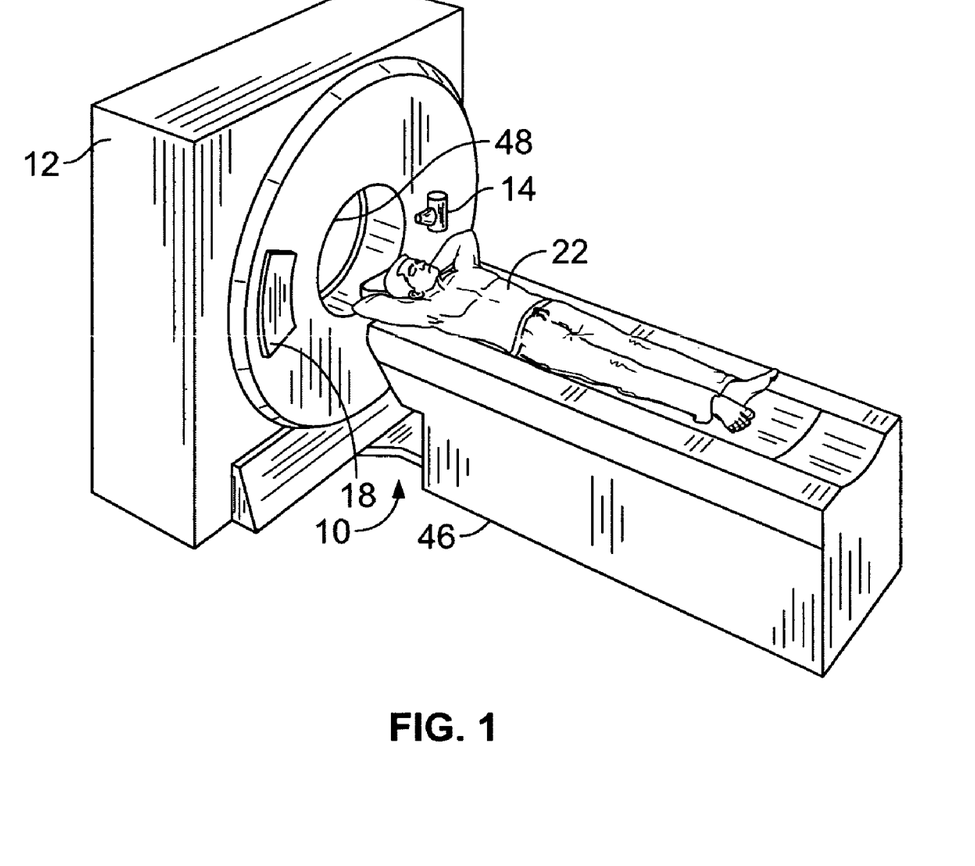
FIG. 1 is a pictorial view of a multi slice volumetric CT imaging system.
Figure 2:
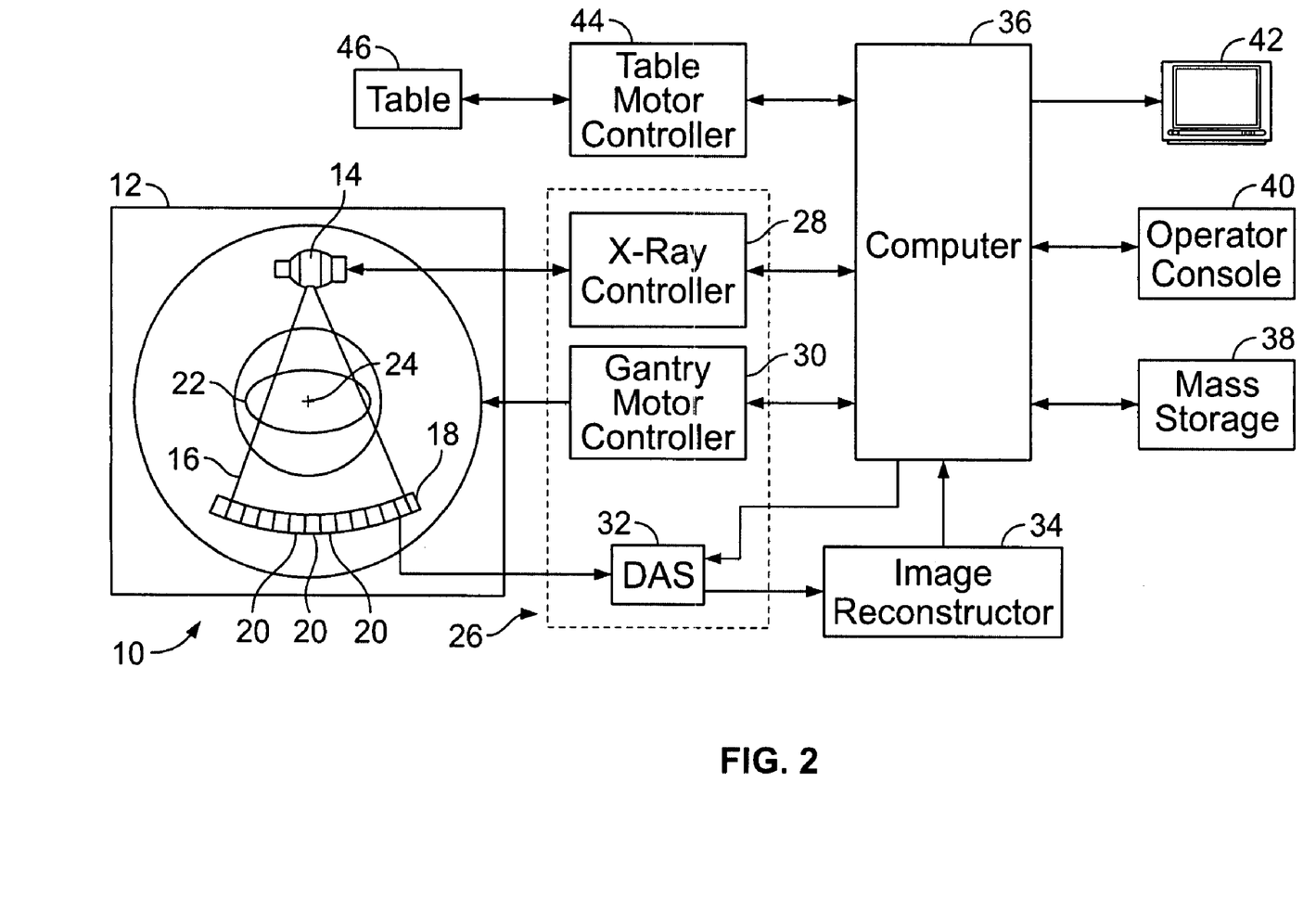
FIG. 2 is a block schematic diagram of the multi slice volumetric CT imaging system illustrated in FIG. 1.

FIG. 1 is a pictorial view of a multi slice volumetric CT imaging system 10. FIG. 2 is a block schematic diagram of CT imaging system 10 illustrated in FIG. 1. In the exemplary embodiment, a CT imaging system 10, is shown as including a gantry 12 representative of a "third generation" CT imaging system. Gantry 12 has a radiation source 14 that projects a cone beam 16 of X-rays toward a detector array 18 on the opposite side of gantry 12.

Detector array 18 is formed by a plurality of detector rows (not shown) including a plurality of detector modules 20 which together sense the projected X-ray beams that pass through an object, such as a medical patient 22. Each detector module 20 includes detector elements (not visible) that produce an electrical signal that represents the intensity of an impinging radiation beam and hence the attenuation of the beam as it passes through object or patient 22. A CT imaging system 10 having a multislice detector array 18 is capable of providing a plurality of images representative of patient 22. Each image of the plurality of images corresponds to a separate "slice" of the volume. The "thickness" or aperture of the slice is dependent upon the thickness of the detector rows.

During a scan to acquire radiation projection data, gantry 12 and the components mounted thereon rotate about a center of rotation 24. FIG. 2 shows only a single row of detector elements (i.e., a detector row). However, multislice detector array 18 includes a plurality of parallel detector rows of detector elements such that projection data corresponding to a plurality of quasi-parallel or parallel slices can be acquired simultaneously during a scan.

Rotation of gantry 12 and the operation of radiation source 14 are governed by a control mechanism 26 of CT imaging system 10. Control mechanism 26 includes a radiation controller 28 that provides power and timing signals to radiation source 14 and a gantry motor controller 30 that controls the rotational speed and position of gantry 12. A data acquisition system (DAS) 32 in control mechanism 26 samples analog data from detector elements and converts the data to digital signals for subsequent processing. An image reconstructor 34 receives sampled and digitized radiation data from DAS 32 and performs high-speed image reconstruction. The reconstructed image is applied as an input to a computer 36 which stores the image in a mass storage device 38.

Computer 36 also receives commands and scanning parameters from an operator via console 40 that has a keyboard. An associated display 42 allows the operator to observe the reconstructed image and other data from computer 36. The operator supplied commands and parameters are used by computer 36 to provide control signals and information to DAS 32, radiation controller 28, and gantry motor controller 30. In addition, computer 36 operates a table motor controller 44 which controls a motorized table 46 to position patient 22 in gantry 12. Particularly, table 46 moves portions of patient 22 through gantry opening 48.

In one embodiment, computer 36 includes a device 50, for example, a floppy disk drive or CD-ROM drive, for reading instructions and/or data from a computer-readable medium, such as a floppy disk or CD-ROM. In another embodiment, computer 36 executes instructions stored in firmware (not shown). Generally, a processor in at least one of DAS 32, reconstructor 34, and computer 36 shown in FIG. 2 is programmed to execute the processes described below. Of course, the method is not limited to practice in CT imaging system 10 and can be utilized in connection with many other types and variations of imaging systems. In one embodiment, computer 36 is programmed to perform functions described herein. Accordingly, as used herein, the term computer is not limited to just those integrated circuits referred to in the art as computers, but broadly refers to computers, processors, microcontrollers, microcomputers, programmable logic controllers, application specific integrated circuits, and other programmable circuits.

Set forth below is a description of an exemplary multislice CT system in accordance with one embodiment of the present invention. Although one embodiment of the system is described in detail below, it should be understood that many alternative embodiments of the inventions are possible. For example, although one particular detector and one particular pre-patient collimator are described, other detectors or collimators could be used in connection with the system, and the present invention is not limited to practice with any one particular type of detector. Specifically, the detector described below includes a plurality of modules and each module includes a plurality of detector cells. Rather than the specific detector described below, a detector which has non-segmented cells along the z-axis, and/or a detector which has multiple modules 20 with multiple elements along the x-axis and/or z-axis joined together in either direction to acquire multislice scan data simultaneously, can be utilized. Generally, the system is operable in a multislice mode to collect one or more slices of data. Axial and helical scans can be performed with the system, and cross section images of a scanned object can be processed, reconstructed, displayed and/or archived.

Figure 3:
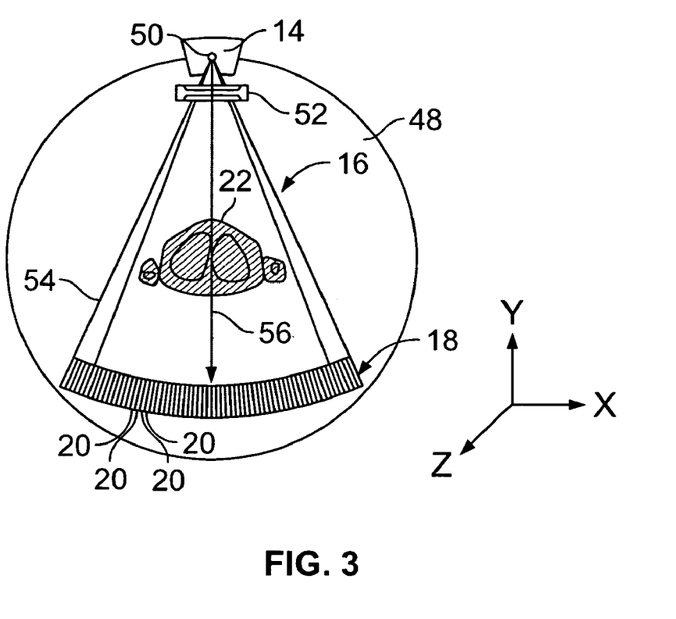
FIG. 3 is an axial view of an exemplary embodiment of the CT imaging system shown in FIG. 1.

FIG. 3 is an axial view of an exemplary embodiment of CT imaging system 10. With respect to the operation of radiation source 14, x-ray beam 16 emanates from a focal spot 50 of radiation source 14. X-ray beam 16 is collimated by pre-patient collimator 52, and a collimated beam 54 is projected toward detector array 18 along a fan beam axis 56 centered within x-ray beam 16.

Detector array 18 and collimator 52 can be configured such that CT imaging system 10 reduces x-ray dosage to patient 22. Particularly, by configuring detector array 18 and dynamically adjusting collimator 52 during a scan, CT imaging system 10 reduces a z-axis dimension of beam 54 to a thickness that facilitates reducing overscan, i.e., exposure to rows outside of the image region.

Figure 4:
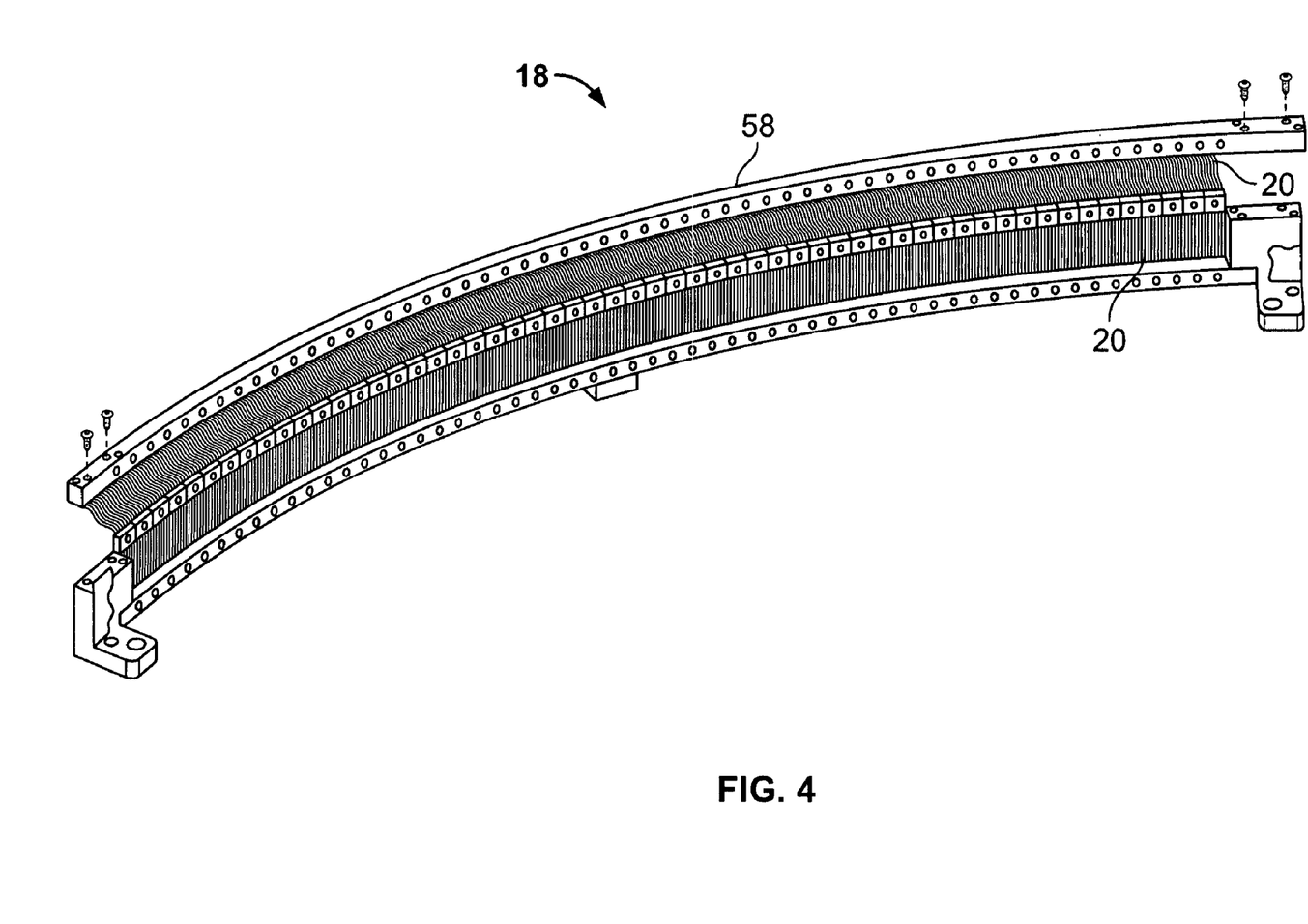
FIG. 4 is a perspective view of an exemplary embodiment of a detector-array, such as the detector array shown in FIG. 2.
Figure 5:
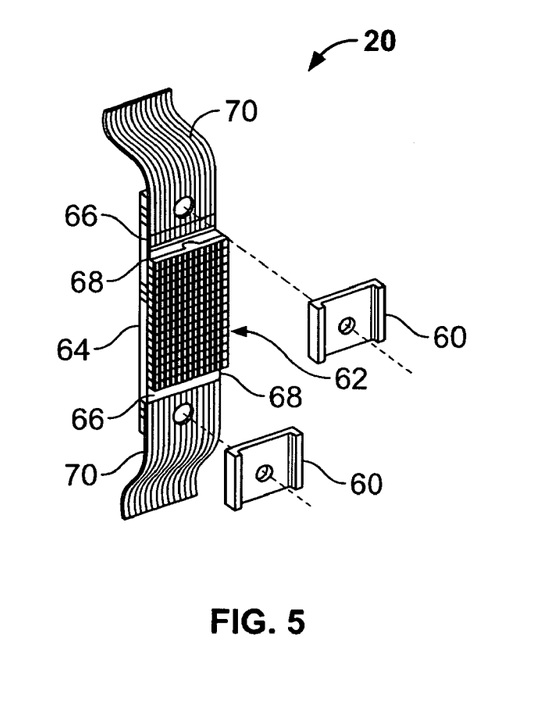
FIG. 5 is an enlarged perspective view of an exemplary detector module that may be used with the detector array shown in FIG. 4.

Particularly with respect to an example detector, FIG. 4 is a perspective view of an exemplary embodiment of a detector array, such as detector array 18 (shown in FIG. 2). FIG. 5 is an enlarged perspective view of an exemplary detector module 20 that may be used with detector array 18. Each detector module 20 is secured to a detector housing 58 by plates 60. Each module 20 includes a multidimensional scintillator array 62 and a high density semiconductor array (not visible). A post patient collimator (not shown) is positioned over and adjacent scintillator array 62 to collimate x-ray beams before such beams impinge upon scintillator array 62. Scintillator array 62 includes a plurality of scintillation elements arranged in an array, and the semiconductor array includes a plurality of photodiodes (not visible) arranged in an identical array. The photodiodes are deposited, or formed on a substrate 64, and scintillator array 62 is positioned over and secured to substrate 64.

Detector module 20 also includes a switch apparatus 66 electrically coupled to a decoder 68. Switch apparatus 66 is a multidimensional semiconductor switch array of similar size as the photodiode array. In one embodiment, switch apparatus 66 includes an array of field effect transistors (not shown) with each field effect transistor (FET) having an input, an output, and a control line (not shown). Switch apparatus 66 is coupled between the photodiode array and DAS 32. Particularly, each switch apparatus FET input is electrically connected to a photodiode array output and each switch apparatus FET output is electrically connected to DAS 32, for example, using flexible electrical cable 70.

Decoder 68 controls the operation of switch apparatus 66 to enable, disable, or combine the outputs of the photodiode array in accordance with a desired number of slices and slice resolutions for each slice. Decoder 68, in one embodiment, is a decoder chip or a FET controller as known in the art. Decoder 68 includes a plurality of output and control lines coupled to switch apparatus 66 and computer 36. Particularly, the decoder outputs are electrically connected to the switch apparatus control lines to enable switch apparatus 66 to transmit the proper data from the switch apparatus inputs to the switch apparatus outputs. The decoder control lines are electrically connected to the switch apparatus control lines and determine which of the decoder outputs will be enabled. Utilizing decoder 68, specific FETs within switch apparatus 66 are enabled, disable, or combined so that specific outputs of the photodiode array are electrically connected to CT system DAS 32. In one embodiment defined as a sixteen slice mode, decoder 68 enables switch apparatus 66 so that all rows of the photodiode array are electrically connected to DAS 32, resulting in sixteen separate, simultaneous slices of data being sent to DAS 32. Of course, many other slice combinations are possible.

In one specific embodiment, detector array 18 includes fifty-seven detector modules 20. The photodiode array and scintillator array 62 each have an array size of sixteen by sixteen. As a result, detector array 18 has sixteen rows and 912 columns (sixteen times fifty-seven modules), which enables sixteen simultaneous slices of data to be collected with each rotation of gantry 12. Of course, the present invention is not limited to any specific array size, and it is contemplated that the array can be larger or smaller depending upon the specific operator needs. Also, detector array 18 may be operated in many different slice thickness and number modes, e.g., one, two, and four slice modes. For example, the FETs can be configured in the four slice mode, so that data is collected for four slices from one or more rows of the photodiode array. Depending upon the specific configuration of the FETs as defined by decoder control lines, various combinations of outputs of the photodiode array can be enabled, disabled, or combined so that the slice thickness may, for example, be 1.25 mm, 2.5 mm, 3.75 mm, or 5 mm. Additional examples include a single slice mode including one slice with slices ranging from 1.25 mm thick to 20 mm thick, and a two slice mode including two slices with slices ranging from 1.25 mm thick to 10 mm thick. Additional modes beyond those described are possible.

Figure 6:
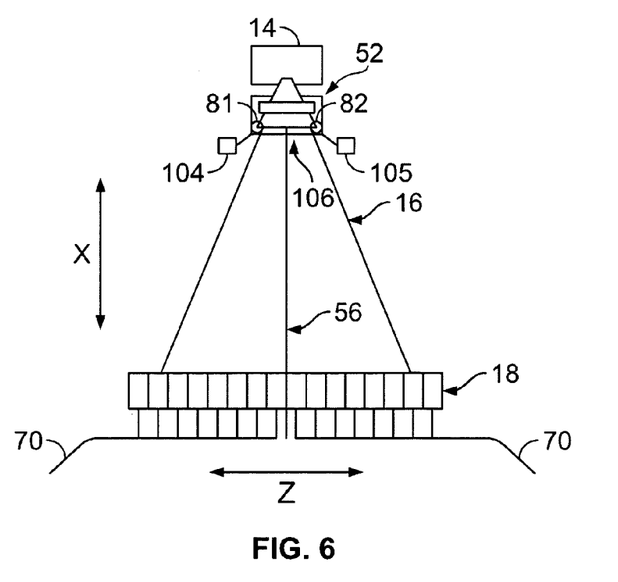
FIG. 6 is a schematic side view of an exemplary embodiment of the CT imaging system shown in FIG. 1.

FIG. 6 is a schematic side view of an exemplary embodiment of CT imaging system 10. Collimator 52 includes a first eccentric cam, shutter cam 81, and a second eccentric cam, tracking cam 82 for adjusting an aperture 106 between them. Shutter cam 81 is located on the trailing side of collimator 52 in a direction of movement of table 46. The position of cams 81 and 82 is controlled by a collimator controller (not shown) which receives its commands from radiation controller 28. Specifically, the collimator controller includes a cam drive or at least one cam motor 104 and/or 105, for altering the position of cams 81 and 82, respectively. In addition, in one embodiment, the collimator controller includes a processing unit, or logic circuitry for controlling the cam drive and exchanging information with radiation controller 28. In an alternative embodiment, the cam drive may be controlled directly by radiation controller 28.

Cams 81 and 82 are positioned on opposing sides of fan beam axis 56 and may be independently adjusted with respect to the spacing between cams 81 and 82 and their location relative to fan beam axis 56. Cams 81 and 82 may be positioned with a single cam drive, or alternatively, each cam may be positioned with a separate cam drive. For example and in one embodiment, separate cam motors 104 and 105 are connected to respective cams 81 and 82 for precisely controlling the position of cams 81 and 82 so that each cam may be independently positioned. In other embodiments, collimator 52 may include additional cams and each cam may be coupled to a separate cam drive, for example cam motor or actuator, for altering the position of the cam. Cams 81 and 82 are fabricated from an x-ray absorbing material, for example, tungsten and are coupled to the cam motors utilizing accurate ball bearings (not shown).

Figure 7:
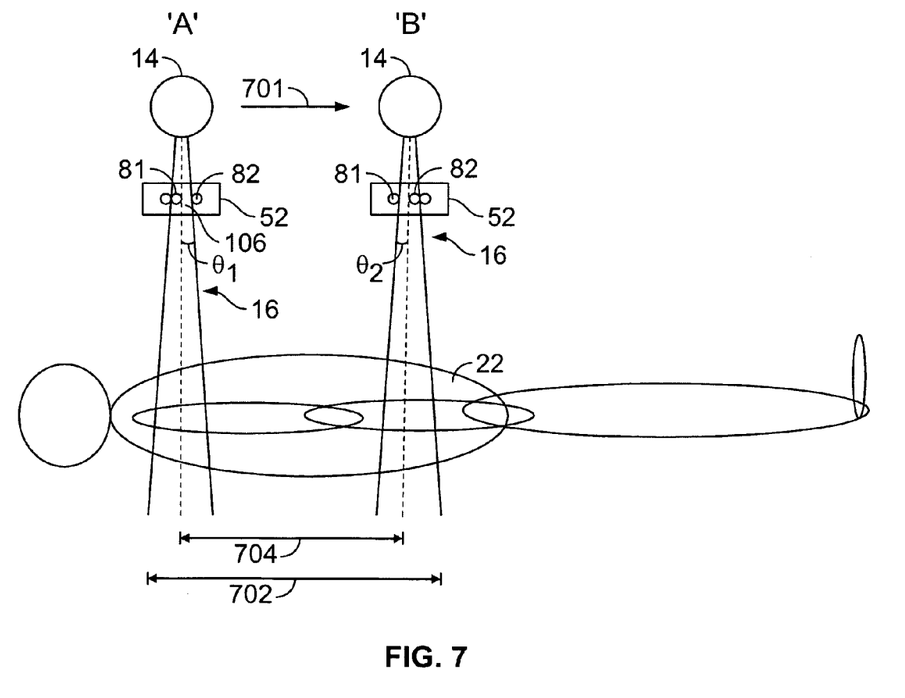
FIG. 7 is a side schematic view of an exemplary embodiment of the CT imaging system shown in FIG. 1.

FIG. 7 is a side schematic view of an exemplary embodiment of CT imaging system 10. The helical overscan length may be reduced by blocking a portion of x-ray beam 16 directed to the unused rows with collimator 52 and unblocking such x-ray beam portion just before the unused rows enter the region to be imaged in a shutter mode. Similarly, the helical overscan length may be reduced by blocking a portion of x-ray beam 16 directed to the unused rows as they spiral out of the image region.

At the beginning of a scan, illustrated by a relative position 'A' in FIG. 7, aperture 106 may be closed as much as possible on the trailing side of the table movement by shutter cam 81, and fully open on the leading side of the table by tracking cam 82. As the scan begins, shutter cam 81 opens up to full aperture 106 at a rate proportional to the table speed. As the scan completes, tracking cam 82 closes down aperture 106 at a rate proportional to the table speed, illustrated by a relative position 'B'. A direction 701 illustrates an exemplary direction of relative position change between radiation source 14 and patient 22 during a helical scan. An angle $\theta_1$ illustrates an x-ray beam 16 angle with cam 81 closed and cam 82 open. An angle $\theta_2$ illustrates an x-ray beam 16 angle with cam 81 open and cam 82 closed. A span 702 indicates a portion of patient 22 exposed to x-rays without cams 81 and 82 operating during a scan. A span 704 indicates a portion of patient 22 that is exposed to x-rays during a scan with cams 81 and 82 operating to block x-rays from reaching the portion of patient 22 that would be within x-ray beam 16, but not in an imaging region of CT imaging system 10. The operation of cams 81 and 82 facilitate reducing radiation to patient 22 by reducing a width of x-ray beam 16 to a width that reduces exposure to portions of patient 22 that are not within the imaging region of CT imaging system 10.

Figure 8:
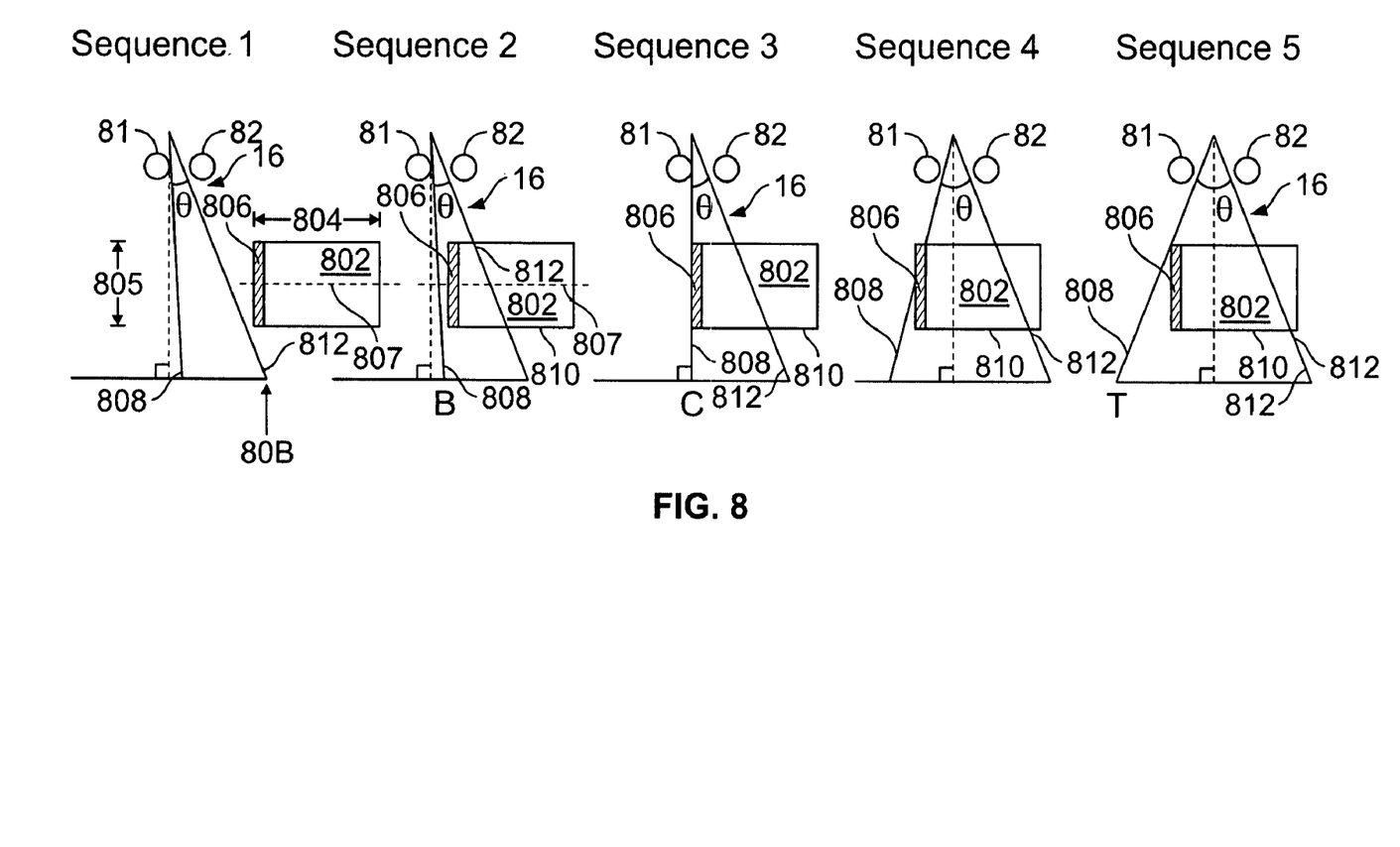
FIG. 8 is a time lapse sequence that illustrates an exemplary shutter mode of operation.

FIG. 8 is a time lapse sequence that illustrates an exemplary shutter mode of operation. Such a shutter mode of operation may include a number of sequences. In the exemplary embodiment, the shutter mode is illustrated using a test object 802 located at a first image position 803. Test object 802 has a thickness 804 and a diameter 805 equal to the image Scan Field of View (SFOV), for example, a diameter of 250 mm or 500 mm. Additionally, in the illustrated embodiment, a longitudinal axis 807 of test object 802 is substantially aligned with axis 24. If patient 22 or, in the exemplary illustration, test object 802, is centered in gantry 12, then diameter 806 is substantially equal to the SFOV. However, in various alternative embodiments, patient 22 or test object may not be centered such that longitudinal axis 807 is not substantially aligned with axis 24. In such a case the SFOV assumption may be modified to account for the longest off center patient radius. Alternatively, if detailed knowledge about the patient size and positioning is available and/or determinable, the sequence of cams 81 and 82 may be modified as a function of angle θ to account for changing patient centering and asymmetry in each view. In sequence 1, shutter cam 81 is closed as much as possible to allow a relatively narrow x-ray beam 16 to just intersect a leading edge 806 of object 802 at (source_to_iso+SFOV/2) wherein source_to_iso is a distance from focal point 90 to an isocenter of object 802. As object 802 moves across x-ray beam 16, it approaches a beam edge 808 defined by shutter cam 81, B in sequence 2. A lower edge 810 of object 802 limits the position of cam 81 until leading edge 806 crosses the centerline of the detector, C in sequence 3. At this point in sequence 4, object 802 is at edge 808 of x-ray beam 16 at (source_to_iso−SFOV/2). Shutter cam 81 continues to open until it is completely open at position T in sequence 5, at which time the tracking loop will begin to control shutter cam 81. The angle θ represents the angle of x-ray beam 16 defined between cams 81 and 82.

The shutter mode of operation may include four regions of operation for the beginning portion of the scan.

| | |
|---|---|
| $t_0 < t < t_B$ | No movement, from sequence 1 to 2 |
| $t_B < t < t_C$ | Slow shutter region, from sequence 2 to 3 |
| $t_C < t < t_T$ | Fast shutter region, from sequence 3 to 5 |
| $t > t_T$ | Tracking, sequence 5 | where, t and z are used to represent time and position with the following subscripts:

$t_0$ is t=0 or when the first view is collected.

$t_B$ is the time during the scan when the object crosses the minimum aperture (B).

$t_C$ is the time when the object crosses the centerline of the detector (C).

$t_T$ is the time when the object crosses the full aperture into the tracking region (T).

B and T will be subscripted with cam, iso, or det to denote the appropriate magnification An approximate cam velocity from B to C may be determined from:

$$v_{BC} = \left( \frac{source\_to\_cam}{source\_to\_iso + \frac{SFOV}{2}} \right) * table\_speed$$

where, source_to_cam is the distance from the source focal point to the z-axis limit of the associated cam; and source_to_iso represents the distance between the source focal point and the isocenter of object 802.

An approximate cam velocity from C to T may be determined from:

$$v_{CT} = \left( \frac{source\_to\_cam}{source\_to\_iso - \frac{SFOV}{2}} \right) * table\_speed$$

Cam position is theoretical minimum allowable cam position to avoid introducing artifacts into the images. Cam must be at or ahead of this position at all times.

| | |
|---|---|
| $0 < t < t_B$ | $B_{cam}$ |
| $t_B < t < t_C$ | $B_{cam} + (t - t_B) * v_{BC}$ |
| $t_C < t < t_T$ | $B_{cam} + (t_C - t_B) * v_{BC} + (t - t_C) * v_{CT}$ |
| $t > t_T$ | $T_{cam}$ |

Timing $$z_0 = T_{iso} * \frac{source\_to\_iso + \frac{SFOV}{2}}{source\_to\_iso}$$

$$z_B = B_{iso} * \frac{source\_to\_iso + \frac{SFOV}{2}}{source\_to\_iso}$$

-continued $$z_T = T_{iso} * \frac{source\_to\_iso - \frac{SFOV}{2}}{source\_to\_iso}$$

$t_B = (z_B + z_0)/\text{table\_speed}$ $t_C = z_0/\text{table\_speed}$ $t_T = (z_T + z_0)/\text{table\_speed}$ It should be noted that z represents an offset. The object does not start at z=0 on the centerline of the detector. Similarly, B is a signed value and in this context it should have a negative value. In various embodiments where longitudinal axis 807 is not substantially aligned with axis 24, the above described equations may be adjusted to account for the simple geometric differences between the position of axis 807 and axis 24.

Figure 9:
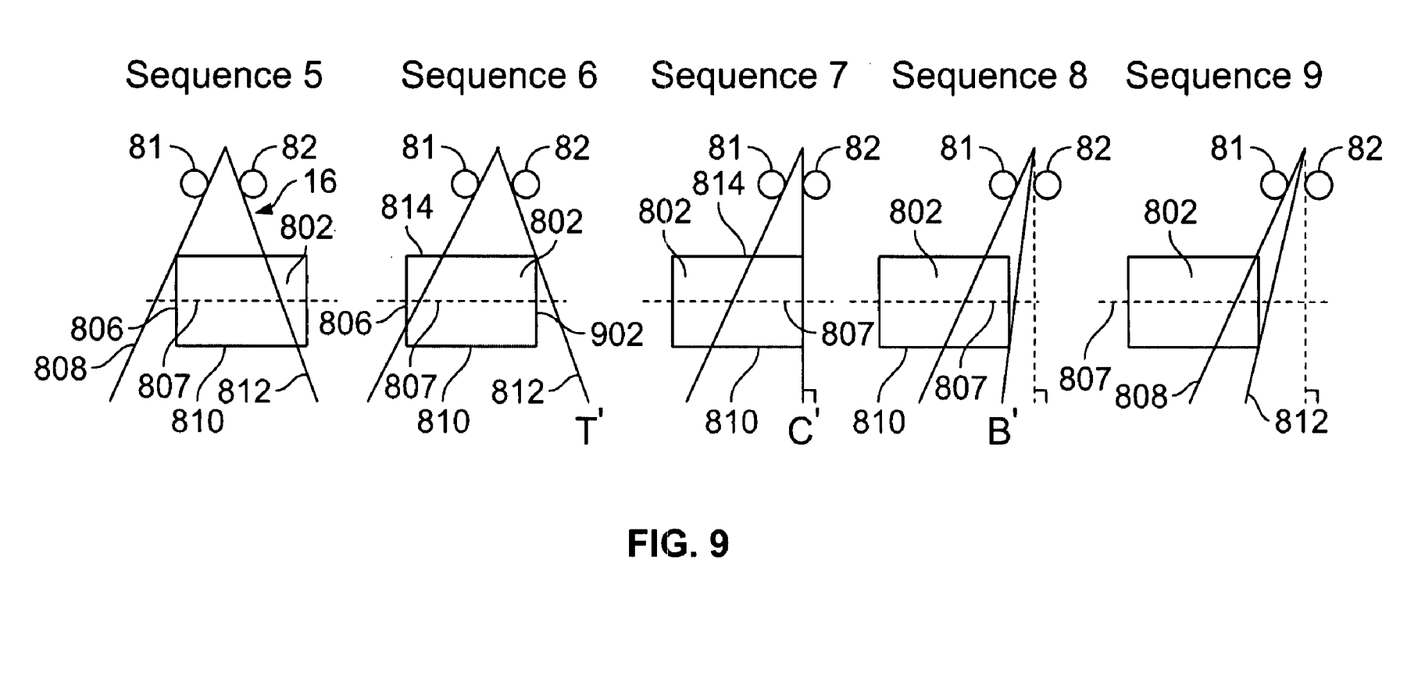
FIG. 9 is a time lapse sequence that illustrates a continuation of the exemplary shutter mode of operation shown in FIG. 8.

FIG. 9 is a time lapse sequence that illustrates a continuation of the exemplary shutter mode of operation shown in FIG. 8. Shuttering is programmed to occur at the end of the scan. Tracking cam 82 stops tracking and essentially functions as shutter cam 81 did during the beginning of the scan except in reverse. Shutter cam 81 remains tracking through the end of the scan. t now represents the time remaining in the scan, and the entire shutter process reverses itself.

| | |
|---|---|
| $t > t_T$ | Tracking |
| $t_C < t < t_T$ | Fast shutter region |
| $t_B < t < t_C$ | Slow shutter region |
| $t_0 < t < t_B$ | No movement |

In sequence 5, shutter cam 81 is completely open and the tracking loop will begin to control shutter cam 81. At this point in Sequence 6, a trailing edge 902 of object 802 is at edge 812 of x-ray beam 16. An upper edge 814 of object 802 limits the position of cam 82 until object 802 crosses the centerline of the detector, C in sequence 7. As object 802 moves across x-ray beam 16, it approaches a beam edge 812 defined by shutter cam 82, B in sequence 2. In sequence 9 shutter cam 82 is closed as much as possible to allow a relatively narrow x-ray beam 16 to just intersect trailing edge 902 of object 802. Object 802 continues through x-ray beam 16 to exit at the end of scan.

The above-described embodiments of an imaging system provide a cost-effective and reliable means for examining a patient. More specifically, the imaging system includes a pair of dynamically positionable cams that shape the x-ray beam in the z-axis such that dosage to the patient is facilitated being reduced.

Exemplary embodiments of imaging system methods and apparatus are described above in detail. The imaging system components illustrated are not limited to the specific embodiments described herein, but rather, components of each imaging system may be utilized independently and separately from other components described herein. For example, the imaging system components described above may also be used in combination with different imaging systems. A technical effect of the various embodiments of the systems and methods described herein include facilitating reducing x-ray dosage to patients during a scan.

While the invention has been described in terms of various specific embodiments, those skilled in the art will recognize that the invention can be practiced with modification within the spirit and scope of the claims.

What is claimed is:

1. A pre-patient collimator for controlling x-ray exposure during a scan with a computed tomography system, the computed tomography system including a patient table translatable along a z-axis, an x-ray source and a detector array, said collimator comprising:
   a first cam configured to shutter an x-ray fan beam, generated by the x-ray source, in a first direction;
   a second cam located on an opposite side of a focal point of the x-ray source from the first cam, said second cam configured to shutter the x-ray fan beam in a second direction, the second direction being opposite from the first direction; and
   a cam drive configured to position at least one of said first cam and said second cam during the scan at a rate proportional to a translation speed of the table.

2. A collimator in accordance with claim 1 wherein said first cam and said second cam are fabricated from a x-ray absorbing material, and said first cam and said second cam are configured to block a portion of an x-ray beam directed towards an object to be imaged to adjust the thickness of the fan beam.

3. A collimator in accordance with claim 2 wherein said cam drive is configured to independently position each said first cam and said second cam.

4. A collimator in accordance with claim 2 wherein said cam drive comprises at least one cam motor.

5. A collimator in accordance with claim 4 wherein said cam drive comprises a cam motor for each said first cam and said second cam.

6. A collimator in accordance with claim 2 wherein said cam drive is configured to modify a fan beam thickness.

7. A system for reducing x-ray exposure in a computed tomography system, the computed tomography system including a patient table translatable along a z-axis, an x-ray source, a detector array comprising a plurality of detector cells extending in the z-axis, and a pre-patient collimator comprising a shutter cam and a tracking cam, said system configured to:
   determine a speed of a patient table along the z-axis; and
   position at least one of the shutter cam and the tracking cam during a scan at a rate proportional to the determined table speed to define a thickness of a fan beam to be directed towards an object to be imaged.

8. A system in accordance with claim 7 wherein said cams are configured to block a portion of an x-ray beam emitted by the x-ray source to adjust the thickness of the fan beam.

9. A method controlling x-ray dosage in a computed tomography system including a patient table translatable along a z-axis and a collimator having a first cam and a second cam that define an aperture, said method comprising:
   opening the first cam at a rate proportional to a translation speed of the table; and
   closing the second cam at a rate proportional to the translation speed of the table.

10. A method in accordance with claim 9 further comprising determining a speed of translation of the table along the z-axis.

11. A method in accordance with claim 9 wherein opening the first cam comprises initiating opening the first cam when a leading edge of an object of interest intersects an edge of an x-ray beam defined by the first cam.

12. A method in accordance with claim 9 wherein opening the first cam comprises opening the first cam at a velocity determined using:

$$\text{velocity} = \left(\frac{\text{source\_to\_cam}}{\text{source\_to\_iso} + \frac{SFOV}{2}}\right) * \text{table\_speed}.$$

13. A method in accordance with claim 9 wherein opening the first cam comprises initiating opening the first cam when a leading edge of an object of interest is coincident with an edge of an x-ray beam defined by the first cam at a velocity determined by:

$$\text{velocity} = \left(\frac{\text{source\_to\_cam}}{\text{source\_to\_iso} - \frac{SFOV}{2}}\right) * \text{table\_speed}.$$

14. A method in accordance with claim 9 wherein closing the second cam comprises initiating closing the second cam when a trailing edge of an object of interest intersects an edge of an x-ray beam defined by the second cam.

15. A method in accordance with claim 9 further comprising fully closing the first cam prior to the beginning of a scan.

16. A method in accordance with claim 9 further comprising fully opening the second cam prior to the beginning of a scan.

17. A method in accordance with claim 9 further comprising maintaining the first cam at a position $B_{cam}$ for a time $t_0 < t < t_B$, wherein to represents a time when the first view is collected, $t_B$ represents a time for a leading edge of an object of interest to intersect the beam edge defined by the first cam when the first cam is fully closed, and wherein $B_{cam}$ is a fully closed position of the first cam.

18. A method in accordance with claim 9 further comprising maintaining the first cam in a position defined by, $B_{cam} + (t - t_B)^* v_{BC}$, for a time, $t_B < t < t_C$, wherein $t_B$ represents a time for a leading edge of an object of interest to intersect the beam edge defined by the first cam when the first cam is fully closed, $B_{cam}$ is a fully closed position of the first cam, and $v_{BC}$ is a velocity of the first cam.

19. A method in accordance with claim 9 further comprising maintaining the first cam in a position defined by, $B_{cam} + (t - t_B)^* v_{BC}$, for a time, $t_B < t < t_C$, wherein $t_B$ represents a time when a leading edge of an object of interest intersects the beam edge defined by the first cam when the first cam is fully closed, $t_C$ represents a time when the object of interest crosses the centerline of the detector (C) $B_{cam}$ is a fully closed position of the first cam, and $v_{BC}$ is a velocity of the first cam.

20. A method in accordance with claim 9 further comprising maintaining the first cam in a position defined by, $B_{cam} + (t_C - t_B)^* v_{BC} + (t - t_C)^* v_{CT}$, for a time, $t_C < t < t_T$, wherein $t_B$ represents a time when a leading edge of an object of interest intersects the beam edge defined by the first cam when the first cam is fully closed, $t_C$ represents a time when the object of interest crosses the centerline of the detector (C), $t_T$ represents a time when the object of interest intersects the beam edge defined by the first cam when the first cam is fully open, $B_{cam}$ is a fully closed position of the first cam, and $v_{BC}$ and $v_{CT}$ are velocities of the first cam.

21. A method in accordance with claim 9 further comprising maintaining the first cam in a fully open position, $B_{cam}$, for a time, $t > t_T$, wherein $t_T$ represents a time when the leading edge of the object of interest intersects the beam edge defined by the first cam when the first cam is fully open.

22. A method in accordance with claim 9 further comprising maintaining the second cam in a fully open position, $T_{cam}$, for a time, $t < t_{T'}$, wherein $t_{T'}$ represents a time when a trailing edge of the object of interest intersects the beam edge defined by the second cam when the second cam is fully open.

23. A method in accordance with claim 9 further comprising maintaining the second cam in a position defined by, $T_{cam} + (t_C - t_{T'})^* v_{TC'}$, for a time, $t_{T'} > t > t_{C'}$, wherein $t_{C'}$ represents a time when the trailing edge of the object of interest crosses the centerline of the detector (C), $t_{T'}$ represents a time when the trailing edge of the object of interest intersects the beam edge defined by the second cam when the second cam is fully open, $T_{cam}$ is a fully open position of the second cam, and $v_{TC}$ is a velocity of the second cam.

24. A method in accordance with claim 9 further comprising maintaining the second cam in a position defined by, $T_{cam} + (t_{B'} - t_{C'})^* v_{B'C'} + (t_{C'} - t_{T'})^* v_{TC'}$, for a time, $t_{C'} < t < t_{B'}$, wherein $t_{B'}$ represents a time when a leading edge of an object of interest intersects the beam edge defined by the first cam when the first cam is fully closed, $t_{C'}$ represents a time when the object of interest crosses the centerline of the detector (C) $B_{cam}$ is a fully closed position of the first cam, and $v_{BC}$ is a velocity of the first cam.

25. A method in accordance with claim 9 further comprising maintaining the first cam at a position $T_{cam}$ for a time $t > t_{B'}$, wherein $t_{B'}$ represents a time for the trailing edge of the object of interest to intersect the beam edge defined by the second cam when the second cam is fully closed, and wherein $T_{cam}$ is a fully closed position of the second cam.

* * * * *

UNITED STATES PATENT AND TRADEMARK OFFICE
CERTIFICATE OF CORRECTION

PATENT NO. : 7,113,570 B2  Page 1 of 1
APPLICATION NO. : 11/053801
DATED : September 26, 2006
INVENTOR(S) : Toth et al.

It is certified that error appears in the above-identified patent and that said Letters Patent is hereby corrected as shown below:

Column 11, line 31, delete "wherein to represents" and insert therefor

-- wherein $t_0$ represents --.

Signed and Sealed this

Twenty-fourth Day of June, 2008

JON W. DUDAS
*Director of the United States Patent and Trademark Office*